(12) United States Patent
Poduslo

(10) Patent No.: US 8,216,787 B2
(45) Date of Patent: Jul. 10, 2012

(54) BIOMARKER FOR SUCCESSFUL AGING WITHOUT COGNITIVE DECLINE

(75) Inventor: Shirley E. Poduslo, North Augusta, GA (US)

(73) Assignee: Medical College of Georgia Research Institute, Inc., Augusta, GA (US)

(*) Notice: Subject to any disclaimer, the term of this patent is extended or adjusted under 35 U.S.C. 154(b) by 0 days.

(21) Appl. No.: 12/759,766

(22) Filed: Apr. 14, 2010

(65) Prior Publication Data

US 2010/0304388 A1 Dec. 2, 2010

Related U.S. Application Data

(60) Provisional application No. 61/217,598, filed on Jun. 2, 2009.

(51) Int. Cl.
*C12Q 1/68* (2006.01)
*C07H 21/04* (2006.01)

(52) U.S. Cl. .................................. 435/6.11; 536/24.3

(58) Field of Classification Search .................. None
See application file for complete search history.

(56) References Cited

U.S. PATENT DOCUMENTS

| | | | |
|---|---|---|---|
| 4,988,617 A | 1/1991 | Landegren | |
| 5,498,531 A | 3/1996 | Jarrell | |
| 2003/0092019 A1* | 5/2003 | Meyer et al. | 435/6 |

OTHER PUBLICATIONS

Juppner Functional properties of the PTH/PTHrP receptor. Bone 1995 vol. 17 No. 2 Supplement 39S-42S.*
Poduslo et al. A genome screen of successful aging without cognitive decline identifies LRP1B by haplotype analysis.*
Gene Card Entry for LRP1 B accessed online at http://www.genecards.org/cgi-bin/carddisp.pl?gene=LRP1B&search=LRP1B on Aug. 8, 2011.*
Hinney, Anke et al. Genome Wide Association Study for Early Onset Extreme Obesity Supports the Role of Fat Mass and Obesity Assoicated Gene Variants. PLOS ONE Dec. 2007 Issue 12 e1361 pp. 1-5.*
The Affymetrix Website https://www.affymetrix.com/analysis/netaffx/mappingfullrecord.affx?pk=GenomeWideSNP5:SNP_A-1824685 accessed on Dec. 28, 2011.*
Brady, et al., "Stroke risk predicts verbal fluency decline in healthy older men: Evidence from the normative aging study.", J Gerontology Series B, 56:340-346 (2001).
Bu, et al., "LRP in amyloid-beta production and metabolism.", Ann NY Acad Sci, 1086:35-53 (2006).
Cam, et al., "The low density lipoprotein receptor-related protein 1B retains beta-amyloid precursor protein at the cell surface and reduces amyloid-beta peptide production.", J Biol Chem, 279(28):29639-29646 (2004).
Falush, et al., "Inference of population structure using multilocus genotype data: linked loci and correlated allele frequencies.", Genetics, 164(4):1567-1587 (2003).
Folstein, et al., "Mini-mental state. A practical method for grading the cognitive state of patients for the clinician.", J Psychiatr Res, 12(3):189-198 (1975).
Huang and Poduslo, "CYP19 haplotypes increase risk for Alzheimer\s disease", S.E., J Med Genet, 43:e42 (2006).
Liu, et al., "The putative tumor suppressor LRP1 B, a novel member of the low density lipoprotein (LDL) receptor family, exhibits both overlapping and distinct properties with the LDL receptor-related protein.", J Biol Chem, 276 (31):28889-28896 (2001).
McKhann, et al., "Clinical diagnosis of Alzheimer's disease: report of the NINCDS-ADRDA Work Group under the auspices of Department of Health and Human Services Task Force on Alzheimer's Disease.", Neurology, 34(7):939-944 (1984).
Perls, et al., "Life-long sustained mortality advantage of siblings of centenarians.", Proc Natl Acad Sci USA, 99(12):8442-8447 (2002).
Purcell, et al., "Genetic Power Calculator: design of linkage and association genetic mapping studies of complex traits.", Bioinformatics, 19(1):149-150 (2003).

* cited by examiner

*Primary Examiner* — Amanda Shaw
(74) *Attorney, Agent, or Firm* — Pabst Patent Group LLP

(57) ABSTRACT

Methods and compositions for determining whether a subject will age without developing cognitive decline are provided. An exemplary method includes detecting one or more allelic variants in a gene encoding low density lipoprotein-related protein 1B. In a preferred embodiment, the detecting step is accomplished by contacting a sample obtained from the subject with a probe that forms a detectable complex with a nucleic acid in the sample containing an allelic variant indicative of aging without developing cognitive decline, wherein detection of the allelic variant in the sample indicates that the subject will age without developing cognitive decline.

2 Claims, No Drawings

US 8,216,787 B2

BIOMARKER FOR SUCCESSFUL AGING WITHOUT COGNITIVE DECLINE

CROSS REFERENCE TO RELATED APPLICATIONS

This application claims benefit of and priority to U.S. Ser. No. 61/217,598 filed on Jun. 2, 2009, which is incorporated by reference in its entirety.

FIELD OF THE INVENTION

The invention is generally related to the field of molecular biology and genetics, in particular to methods and compositions for detecting allelic variants indicative of the ability to age without cognitive decline.

BACKGROUND OF THE INVENTION

A gradual decline in physiological functions as well as susceptibility to age-related diseases, such as cardiovascular disease and dementia, occurs during normal aging. However, there are seniors who escape these age-related diseases. Moreover, there are seniors who are free of cognitive decline into and through very late old age. Very long life has a strong genetic component as centenarians cluster in families and their siblings are likely to live past age 85 (Perls, T., et al., Proc Natl Acad Sci USA, 99:8442-8447 (2002). Of particular interest are seniors who are over the age of 85 with preserved cognition.

Therefore it is an object of the invention to provide biomarkers that can identify subjects that have the ability to age without cognitive decline.

It is another object of the invention to provide genetic markers and methods for using the genetic markers for the identification of subjects that can age without cognitive decline.

SUMMARY OF THE INVENTION

Methods and compositions for determining whether a subject will age without developing cognitive decline are provided. An exemplary method includes detecting one or more allelic variants in a gene encoding low density lipoprotein-related protein 1B. In a preferred embodiment, the detecting step is accomplished by contacting a sample obtained from the subject with a probe that forms a detectable complex with a nucleic acid in the sample containing an allelic variant indicative of aging without developing cognitive decline, wherein detection of the allelic variant in the sample indicates that the subject will age without developing cognitive decline.

Preferred allelic variants include, but are not limited to one or more of the following SNPs: rs12474609; rs10201482; rs980286; rs6732847; rs12053560; rs6748626; rs13016717; rs1346641; rs10928081; rs1247461; rs716000; rs716001; rs16845065; rs11888460; rs11904038; rs130087735, where the presence of one or more of these SNPs is indicative that the subject is more likely than not to age without cognitive decline. Another embodiment provides the following allelic variants that are indicative of the ability to age without cognitive decline: a "A" allele at rs12474609; a "G" allele at rs10201482; a "G" allele at rs980286; a "C" allele at rs6732847; a "T" allele at rs12053560, a "G" allele at rs6748626; an "A" allele at rs13016717; a "T" allele at rs1346641; a "C" allele at rs10928081; a "A" allele at rs12474609; a "G" allele at rs716000; a "C" allele at rs716001; a "G" allele at rs10201482; a "G" allele at rs980286; a "G" allele at rs16845065; a "T" allele at rs11888460; a "C" allele at rs11904038 and a "G" allele at rs13007735.

Preferred haplotypes that are indicative of the ability to age without cognitive decline include, but are not limited to: rs12474609: rs10201482: rs980286: A:G:G; rs6732847: rs12053560: rs6748626:C:T:G; rs13016717: rs1346641: rs10928081: rs12474609:A:T:C:A; rs716000: rs716001: rs10201482: rs980286:G:C:G:G; or rs16845065: rs11888460: rs11904038: rs13007735:G:T:C:G, wherein the presence of one or more of the haplotypes is indicative that the subject will more likely than not age without cognitive decline.

Methods for using the disclosed genetic markers to identify, or assist in the identification of subjects that are able to age without cognitive decline are provided. The methods include the steps of detecting the presence or absence of one or more of the disclosed genetic markers in a biological sample obtained from a subject. The detecting step can include determining whether or not the subject is heterozygous or homozygous for the genetic marker.

Detection of the disclosed genetic markers can be used in combination with one or more additional diagnostic approaches for identifying subjects with the ability to age without cognitive decline relative to a control. Suitable diagnostic methods include, but are not limited to mental status exams, imaging procedures, and the detection of additional genetic markers.

Kits and systems for detecting the disclosed genetic markers are also provided. The kits can include packaged probe and primer sets, arrays of nucleic acid molecules, or beads that contain one or more probes, primers, or other detection reagents. The kits may additionally contain other components necessary to carry out a reaction or assay. In other embodiments, the kits are compartmentalized kits which contain reagents in separate containers.

Also provided are methods for using the disclosed genetic markers as research tools to identify additional genetic markers for the ability to age without cognitive decline using linkage disequilibrium analysis.

DETAILED DESCRIPTION OF THE INVENTION

I. Definitions

As used herein, the term "allele" refers to one of a pair or series, of forms of a gene or non-genic region that occur at a given locus in a chromosome. In a normal diploid cell there are two alleles of any one gene (one from each parent), which occupy the same relative position (locus) on homologous chromosomes. Within a population there may be more than two alleles of a gene. SNPs also have alleles, i.e., the two (or more) nucleotides that characterize the SNP.

As used herein, the term "linkage disequilibrium" or "LD" refers to the situation in which the alleles for two or more loci do not occur together in individuals sampled from a population at frequencies predicted by the product of their individual allele frequencies. Markers that are in LD do not follow Mendel's second law of independent random segregation. LD can be caused by any of several demographic or population artifacts as well as by the presence of genetic linkage between markers. However, when these artifacts are controlled and eliminated as sources of LD, then LD results directly from the fact that the loci involved are located close to each other on the same chromosome so that specific combinations of alleles for different markers (haplotypes) are inherited together. Markers that are in high LD can be assumed to be located near each other and a marker or haplotype that is in high LD with a genetic trait can be assumed to be located near the gene that affects that trait.

As used herein, the term "locus" refers to a specific position along a chromosome or DNA sequence. Depending upon context, a locus could be a gene, a marker, a chromosomal band or a specific sequence of one or more nucleotides.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

As used herein, the term "genotype" refers to a set of alleles at a specified locus or loci.

As used herein, the term "single nucleotide polymorphism (SNP)" refers to a variation of a single nucleotide. This includes the replacement of one nucleotide by another and deletion or insertion of a single nucleotide. Typically, SNPs are bi-allelic markers although tri- and tetra-allelic markers also exist. For example, SNP AC may include allele C or allele A. Thus, a nucleic acid molecule having SNP AC may include a C or A at the polymorphic position.

As used herein, the term "haplotype" refers to the allelic pattern of a group of (usually contiguous) DNA markers or other polymorphic loci along an individual chromosome or double helical DNA segment. Haplotypes identify individual chromosomes or chromosome segments. The presence of shared haplotype patterns among a group of individuals implies that the locus defined by the haplotype has been inherited, identical by descent (IBD), from a common ancestor. In some instances, a specific allele or haplotype may be associated with susceptibility to a disorder or condition of interest, e.g., late-onset Alzheimer's disease. The term "haplotype" is specifically used herein to refer to a combination of SNP alleles, e.g., the alleles of the SNPs found together on a single DNA molecule. In specific embodiments, the SNPs in a haplotype are in linkage disequilibrium with one another.

As used herein the term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

As used herein, a "genetic marker" is an identifiable DNA sequence that is variable (polymorphic) for different individuals within a population. Exemplary genetic markers include SNPs and haplotypes.

As used herein, the terms "probe" or "primer" refer to a nucleic acid or oligonucleotide that forms a hybrid structure with a sequence in a target region of a nucleic acid due to complementarity of the probe or primer sequence to at least one portion of the target region sequence.

The terms "individual", "host", "subject", and "patient" are used interchangeably herein, and refer to a mammal, including, but not limited to, humans, rodents such as mice and rats, and other laboratory animals.

II. Genetic Markers for with Cognitive Decline

Genetic markers for determining whether a person is more likely than not to age successfully without cognitive decline are provided. It has been discovered that alterations in the gene locus for low density lipoprotein receptor-related protein (LRP1B) are associated with successful aging without cognitive decline. The term "cognitive decline" refers to a score of $\leq 25$ on the MMSE or Mini Mental State Examination (Folstein, et al., *J Psychiatr Res,* 12: 189-198 (1975)). The term "without cognitive decline refers to a MMSE score of $\geq 26$. The MMSE scored can be taken at an age greater than 40, 45, 50, 55, 60, 65, 70, 75, 80, or 85 years of age.

A. LRP1B

LRP1B belongs to the low density lipoprotein receptor gene family; it is located on chromosome 2q21.2. The gene is large, 1,906.41 kb, contains 93 introns, and 5 alternatively spliced mRNA's (AceView). The cDNA sequence is found at NCBI Accession No. AF176832. The genomic sequence is found at NCBI Accession No. NT_022135. Of the three spliced mRNA's which encode good proteins, the "a" form is 16,535 bp, and the protein product is 4,636 aa. The protein has 4 extracellular ligand-binding domains which have different numbers of cysteine-rich ligand-binding repeats; it also has clusters of epidermal growth factor precursor repeats, and (F/Y)WXD spacer repeats. The 89 exons of LRP1B are nearly identical to those in LRP (low density lipoprotein receptor-related protein). The extra exons include exon 68 which encodes an additional ligand-binding repeat in domain IV, and exon 90, which encodes a 33 amino acid insertion in the cytoplasmic tail (Liu, C-X, et al., *J Biol Chem,* 276: 28889-28896 (2001)).

LRP is widely expressed, has multiple functions, and interacts with multiple ligands. While LRP is expressed in liver, brain, and lung, LRP is most abundant in brain, thyroid, and salivary glands (Liu, C-X, et al., *J Biol Chem,* 276: 28889-28896 (2001)).

Both LRP and LRPIB are expressed at the cell surface and both bind and internalize similar ligands. However, the internalization rate is 15-fold slower or 80% less efficient for LRPIB when compared with LRP (Cam, J A, et al., *J Biol Chem,* 279:29639-29646 (2004)). It has been shown that the protein product of LRP1B interacts with the β-amyloid precursor protein (APP) on the cell surface and binds soluble APP (Bu, G., et al., *Ann NY Acad Sci,* 1086:35-53 (2006)). There is a threefold accumulation of APP at the cell surface, due to the slower endocytosis rate of the protein product of LRPIB. This accumulation of APP results in decreased production of Aβ40 (amyloid-β peptide) and Aβ42 (Cam, J A, et al., *J Biol Chem,* 279:29639-29646 (2004)). If the haplotypes described in our study are involved with the decreased production of Aβ42 in successful aging, LRP1B may become a new therapeutic approach for the treatment of Alzheimer's disease.

B. LRP1B Gene Alterations

The disclosed genetic markers for successful aging without cognitive decline include alterations in the LRP1B gene. Suitable alterations include, but are not limited to, polymorphisms, mutations, deletions, rearrangements, and/or insertions in the coding and/or non-coding regions of the LRP1B, alone or in combination. Preferred allelic variants or SNPs of significance are located primarily in intron 18 which is 30,219 bp.

Mutations more specifically include point mutations. Deletions may encompass any region of two or more residues in a coding or non-coding portion of the gene locus, such as from two residues up to the entire gene or locus. Typical deletions affect smaller regions, such as domains (introns) or repeated sequences or fragments of less than about 50 consecutive base pairs, although larger deletions may occur as well. Insertions may encompass the addition of one or several residues in a coding or non-coding portion of the gene locus. Insertions may typically comprise an addition of between 1 and 50 base pairs in the gene locus. Rearrangement includes inversion of sequences. The LRP gene locus alteration may result in the creation of stop codons, frameshift mutations, amino acid substitutions, particular RNA splicing or processing, product instability, truncated polypeptide production, etc. The alteration may result in the production of a LRP1B polypeptide with altered function, stability, targeting or structure. The alteration may also cause a reduction or an increase in protein expression. The alteration may be determined at the level of the LRP1B DNA, RNA or polypeptide.

1. Single Nucleotide Polymorphisms

In some embodiments, the genetic markers include one or more single nucleotide polymorphisms (SNPs) within the LRP1B gene. SNPs are single base positions in DNA at which different alleles, or alternative nucleotides exist in a population. Approximately 90% of all polymorphisms in the human genome are SNPs. The SNP position is usually preceded by and followed by highly conserved sequences of the allele (e.g., sequences that vary in less than 1/100 or 1/1000 members of the populations). An individual may be homozygous or heterozygous for an allele at each SNP position.

A SNP may arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP may also be a single base insertion or deletion variant referred to as an "indel" (Weber, et al., *Am. J. Hum. Genet.*, 71 (4):854-62 (2002)).

In certain embodiments, the genetic markers include one or more of the following SNPs in any combination, referred to by their dbSNP Database RS ID numbers: rs12474609, rs10201482, and rs980286. These SNPs are listed in order as read from the forward strand and not the reverse coding strand, and are located at the following physical positions on chromosome 2q22.1, respectively: 141,446,369; 141,446,369; and 141,447,731.

In preferred embodiments, the genetic markers include one or more of the following alleles of the above-listed SNPs in any combination: a "A" allele at rs12474609; a "G" allele at rs10201482; and a "G" allele at rs980286.

Other SNPs include, but are not limited to: a "C" allele at rs6732847; a "T" allele at rs12053560, and a "G" allele at rs6748626.

Another embodiment provides one or more SNPs including" an "A" allele at rs13016717; a "T" allele at rs1346641; a "C" allele at rs10928081; and a "A" allele at rs12474609.

Still another embodiment provides one or more of the following SNPs: a "G" allele at rs716000; a "C" allele at rs716001; a "G" allele at rs10201482; and a "G" allele at rs980286.

Yet another embodiment provides one or more of the following SNPs: a "G" allele at rs16845065; a "T" allele at rs11888460; a "C" allele at rs11904038 and a "G" allele at rs13007735.

2. Haplotypes

In other embodiments, the genetic marker is a haplotype that includes two or more of the above-referenced SNPs in any combination. In a preferred embodiment, the haplotype is rs12474609: rs10201482: rs980286: A:G:G. This haplotype can also be expressed as 12474609_A: rs10201482_G: rs980286_G: A:G:G.

Additional haplotypes include Other SNPs include, but are not limited to: rs6732847: rs12053560: rs6748626:C:T:G.

Another embodiment provides the following haplotype: rs13016717: rs1346641: rs10928081: rs12474609:A:T:C:A.

Still another embodiment provides the following haplotype: rs716000: rs716001: rs10201482: rs980286:G:C:G:G.

Yet another embodiment provides the following haplotype: rs16845065: rs11888460: rs 11904038: rs13007735:G:T:C:G.

III. Methods for Using Genetic Markers for Assessing Survivability without Cognitive Decline A. Diagnosis The disclosed genetic markers can be used to identify, or assist in the identification of subjects that are more likely than not to survive to an age greater than 40, 45, 50, 55, 60, 65, 70, 75, 80, or 85 years of age without cognitive decline. A subject identified as having an increased probability of aging without cognitive decline has the genetic variations described above.

Methods of diagnosing, or assisting in the diagnosis of a subject that is more likely to age without cognitive decline include the steps of detecting the presence or absence of one or more of the disclosed genetic markers in a biological sample obtained from the subject. Any biological sample that contains the DNA of the subject to be assayed can be employed, including tissue samples and blood samples, with nucleated blood cells being a particularly convenient source. The DNA may be isolated from the biological sample prior to testing the DNA for the presence or absence of the disclosed genetic markers. Methods for detecting the disclosed genetic markers are provided below.

In one embodiment, the DNA of the biological sample is tested for the presence or absence of one or more of the following SNPs in any combination: rs12474609; rs10201482; rs980286; rs6732847; rs12053560; rs6748626; rs13016717; rs1346641; rs10928081; rs1247461; rs716000; rs716001; rs16845065; rs11888460; rs11904038; rs130087735, where the presence of one or more of these SNPs is indicative that the subject is more likely than not to age without cognitive decline. For example, the DNA may be tested for the presence or absence of any combination of 1, 2, 3, 4, 5, 6, 7, 8, 9, 10, 11, 12, or all of these SNPs.

In other embodiments, the DNA of the biological sample is tested for the presence or absence of one or more of the following alleles in any combination: a "A" allele at rs12474609; a "G" allele at rs10201482; a "G" allele at rs980286; a "C" allele at rs6732847; a "T" allele at rs12053560, a "G" allele at rs6748626; an "A" allele at rs13016717; a "T" allele at rs1346641; a "C" allele at rs10928081; a "A" allele at rs12474609; a "G" allele at rs716000; a "C" allele at rs716001; a "G" allele at rs10201482; a "G" allele at rs980286; a "G" allele at rs16845065; a "T" allele at rs11888460; a "C" allele at rs11904038 and a "G" allele at rs13007735, wherein the presence of one or more of these alleles is indicative that the subject is more likely than not able to age without cognitive decline. For example, the DNA may be tested for the presence or absence of any combination of 1, 2, 3, 4, 5, 6, 7, 8, 9, or all of these alleles.

In another embodiment, the DNA of the biological sample is tested for the presence or absence of the one or more of the following haplotypes: rs12474609: rs10201482: rs980286: A:G:G; rs6732847: rs12053560: rs6748626:C:T:G; rs13016717: rs1346641: rs10928081: rs12474609:A:T:C:A; rs716000: rs716001: rs10201482: rs980286:G:C:G:G; or rs16845065: rs11888460: rs11904038: rs13007735:G:T:C:

G, wherein the presence of one or more of the haplotypes is indicative that the subject will more likely than not age without cognitive decline.

The detecting step can include determining whether the subject is heterozygous or homozygous for the genetic marker. The step of detecting the presence or absence of the genetic marker can include the step of detecting the presence or absence of the marker in both chromosomes of the subject (i.e., detecting the presence or absence of one or two alleles containing the marker or functional polymorphism). More than one copy of a genetic marker (i.e., subjects homozygous for the genetic marker) can indicate a greater likelihood that the subject will age without cognitive decline.

B. Methods for Detecting SNPs and Haplotypes

The process of determining which specific nucleotide (i.e., allele) is present at each of one or more SNP positions, such as a disclosed SNP position in the LRP1B gene locus, is referred to as SNP genotyping. Methods for SNP genotyping are generally known in the art (Chen et al., *Pharmacogenomics J.*, 3(2):77-96 (2003); Kwok, et al., *Curr. Issues Mol. Biol.*, 5(2):43-60 (2003); Shi, *Am. J. Pharmacogenomics*, 2(3):197-205 (2002); and Kwok, *Annu. Rev. Genomics Hum. Genet.*, 2:235-58 (2001)).

SNP genotyping can include the steps of collecting a biological sample from a subject (e.g., sample of tissues, cells, fluids, secretions, etc.), isolating genomic DNA from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

The neighboring sequence can be used to design SNP detection reagents such as oligonucleotide probes and primers. Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

SNPs can be scored by direct DNA sequencing. A variety of automated sequencing procedures can be utilized, including sequencing by mass spectrometry. Methods for amplifying DNA fragments and sequencing them are well known in the art.

Other suitable methods for detecting polymorphisms include methods in which protection from cleavage agents is used to detect mismatched bases in RNA/RNA or RNA/DNA duplexes (Myers et al., *Science*, 230:1242 (1985); Cotton, et al., *PNAS*, 85:4397 (1988); and Saleeba, et al., *Meth. Enzymol.*, 217:286-295 (1992)), comparison of the electrophoretic mobility of variant and wild type nucleic acid molecules (Orita et al., *PNAS*, 86:2766 (1989); Cotton, et al, *Mutat. Res.*, 285:125-144 (1993); and Hayashi, et al., *Genet. Anal. Tech. Appl.*, 9:73-79 (1992)), and assaying the movement of polymorphic or wild-type fragments in polyacrylamide gels containing a gradient of denaturant using denaturing gradient gel electrophoresis (DGGE) (Myers et al., *Nature*, 313:495 (1985)). Sequence variations at specific locations can also be assessed by nuclease protection assays such as RNase and S1 protection or chemical cleavage methods.

In one embodiment, SNP genotyping is performed using the TaqMan® assay, which is also known as the 5' nuclease assay. The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5'-most and the 3'-most ends, respectively, or vice versa. Alternatively, the reporter dye may be at the 5'- or 3'-most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Another method for genotyping SNPs is the use of two oligonucleotide probes in an OLA (U.S. Pat. No. 4,988,617). In this method, one probe hybridizes to a segment of a target nucleic acid with its 3'-most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization—Time of Flight) mass spectrometry technology is useful for extremely precise determinations of molecular mass, such as SNPs. Numerous approaches to SNP analysis have been developed based on mass spectrometry. Exemplary mass spectrometry-based methods of SNP genotyping include primer extension assays, which can also be utilized in combination with other approaches, such as traditional gel-based formats and microarrays.

Typically, the primer extension assay involves designing and annealing a primer to a template PCR amplicon upstream (5') from a target SNP position. A mix of dideoxynucleotide triphosphates (ddNTPs) and/or deoxynucleotide triphosphates (dNTPs) are added to a reaction mixture containing template (e.g., a SNP-containing nucleic acid molecule which has typically been amplified, such as by PCR), primer, and DNA polymerase. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the SNP position. If the primer is several nucleotides removed from the target SNP position, the only limitation is that the template sequence between the 3' end of the primer and the SNP position cannot contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer. The extended primers can then be purified and analyzed by MALDI-TOF mass spectrometry to determine the identity of the nucleotide present at the target SNP position.

Other methods that can be used to genotype the SNPs include single-strand conformational polymorphism (SSCP), and denaturing gradient gel electrophoresis (DGGE). SSCP identifies base differences by alteration in electrophoretic migration of single stranded PCR products. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel.

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis.

C. SNP Detection Kits

Detection reagents can be developed and used to assay the disclosed SNPs individually or in combination, and such detection reagents can be readily incorporated into a kit or system format. The terms "kits" and "systems", as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more of the disclosed SNPs are provided. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment, kits are provided which contain the necessary reagents to carry out one or more assays to detect one or more of the disclosed SNPs. In an exemplary embodiment, SNP detection kits/systems are in the form of nucleic acid arrays, or compartmentalized kits, including microfluidic/lab-on-a-chip systems.

SNP detection kits may contain, for example, one or more probes, or pairs of probes, that hybridize to a nucleic acid molecule at or near each target SNP position. Multiple pairs of allele-specific probes may be included in the kit/system to simultaneously assay large numbers of SNPs. In some kits, the allele-specific probes are immobilized to a substrate such as an array or bead.

The terms "arrays", "microarrays", and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate.

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized. Probes can be attached to a solid support in an ordered, addressable array.

A microarray can be composed of a large number of unique, single-stranded polynucleotides, usually either synthetic antisense polynucleotides or fragments of cDNAs, fixed to a solid support. Typical polynucleotides are about 6-60 nucleotides in length, or about 15-30 nucleotides in length, or about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, exemplary probe lengths can be, for example, about 15-80 nucleotides in length, or about 50-70 nucleotides in length, or about 55-65 nucleotides in length, or about 60 nucleotides in length. The microarray or detection kit can contain polynucleotides that cover the known 5' or 3' sequence of a gene/transcript or target SNP site, sequential polynucleotides that cover the full-length sequence of a gene/transcript; or unique polynucleotides selected from particular are as along the length of a target gene/transcript sequence. Polynucleotides used in the microarray or detection kit can be specific to a SNP or SNPs of interest (e.g., specific to a particular SNP allele at a target SNP site, or specific to particular SNP alleles at multiple different SNP sites).

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated. Such high stringency conditions may be preferable when using, for example, nucleic acid arrays of allele-specific probes for SNP detection. In some embodiments, the arrays are used in conjunction with chemiluminescent detection technology.

A polynucleotide probe can be synthesized on the surface of the substrate by using a chemical coupling procedure and an inkjet application apparatus, as described in PCT Publication No. WO 95/251116. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures.

Methods for using such arrays or other kits/systems, to identify SNPs and haplotypes disclosed herein in a test sample are provided. Such methods typically involve incubating a test sample of nucleic acids with an array comprising one or more probes corresponding to at least one SNP position of the present invention, and assaying for binding of a nucleic acid from the test sample with one or more of the probes. Conditions for incubating a SNP detection reagent (or a kit/system that employs one or more such SNP detection reagents) with a test sample vary. Incubation conditions depend on such factors as the format employed in the assay, the detection methods employed, and the type and nature of the detection reagents used in the assay.

A SNP detection kit/system can include components that are used to prepare nucleic acids from a test sample for the subsequent amplification and/or detection of a SNP-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue specimens.

Another form of kit is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more of the disclosed SNPs, one or more containers which contain wash reagents (such as phosphate buffered saline, Tris-buffers, etc.), and one or more containers which contain the reagents used to reveal the presence of the bound probe or other SNP detection reagents. The kit can optionally further include compartments and/or reagents for, for example, nucleic acid amplification or other enzymatic reactions such as primer extension reactions, hybridization, ligation, electrophoresis (e.g., capillary electrophoresis), mass spectrometry, and/or laser-induced fluorescent detection. The kit may also include instructions for using the kit.

Microfluidic devices may also be used for analyzing SNPs. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more of the disclosed SNPs. For genotyping SNPs, an exemplary microfluidic system may integrate, for example, nucleic acid amplification, primer extension, capillary electrophoresis, and a detection method such as laser induced fluorescence detection.

D. Identification of Additional Genetic Markers

The disclosed genetic markers are useful for identifying additional genetic markers associated with aging without cognitive decline. For example, the SNPs disclosed above can be used to identify additional SNPs that are in linkage disequilibrium. Indeed, any SNP in linkage disequilibrium with a first SNP associated with aging without cognitive decline will be associated with aging without cognitive decline. Once the association has been demonstrated between a given SNP and aging without cognitive decline, the discovery of additional SNPs associated with aging without cognitive decline can be of great interest in order to increase the density of SNPs in this particular region.

Methods for identifying additional SNPs and conducting linkage disequilibrium analysis are well known in the art. For example, identification of additional SNPs in linkage disequilibrium with the SNPs disclosed herein can involve the steps of: (a) amplifying a fragment from the genomic region comprising or surrounding a first SNP from a plurality of individuals; (b) identifying of second SNPs in the genomic region harboring or surrounding said first SNP; (c) conducting a linkage disequilibrium analysis between said first SNP and second SNPs; and (d) selecting said second SNPs as being in linkage disequilibrium with said first marker.

E. Additional Diagnostic Methods to be Used in Combination

Detection of the disclosed genetic markers may be used in combination with one or more additional diagnostic approaches for identifying subjects that are more likely than not able to age without cognitive decline. For example, subjects can be screened for additional genetic markers in addition to the genetic markers disclosed herein. Subjects can also be subjected to a mental status exam, such as the Mini Mental State Exam (MMSE) to assess memory, concentration, and other cognitive skills. The subject an also be subjected to imaging procedures, such as a CT scan, an MRI, or a PET scan to identify changes in brain structure or size indicative of Alzheimer's disease.

Another embodiment provides a computer-implemented system for determining whether a subject will age without cognitive decline. The system includes a means for determining the presence of one or more allelic variants in a gene encoding low density lipoprotein-related protein 1B from a sample obtained from a subject. This can include a computer-implemented mass spectroscopy device, a computer-implemented fluorometer, or a computer implemented fluorescence reader. The system optionally includes a means for communicating the detected allelic variants for example through a display or by generating a report.

EXAMPLE

Example 1

Haplotypes in the LRP1B Gene are Significant for Successful Aging without Cognitive Decline A genome-wide scan of the seniors with successful aging without cognitive decline versus late-onset Alzheimer's disease was undertaken, using the Affymetrix GeneChip® Human Mapping 500 K Array set. A significant set of SNPs in the gene, the low density lipoprotein receptor-related protein 1B (LRP1B), was identified, after Bonferroni correction. Additional SNPs in the LRP1B gene were analyzed and several haplotypes were found to be significant for successful aging without cognitive decline.

Methods and Materials

Subjects with Successful Aging without Cognitive Decline

The successful aging without cognitive decline subjects (SA) were recruited from retirement villages and through community events. To be eligible, the subjects were 85 years or older and had an MMSE>26. (The MMSE or Mini Mental State Examination is a tool that assesses mental status (Folstein, M. F., et al., *J Psychiatr Res*, 12:189-198 (1975)). The MMSE consists of 11 questions which tests five areas of cognitive function. While the maximum score is 30, the score of $\leq 25$ indicates cognitive impairment.) In addition, the subjects did not have any major illnesses, such as cardiovascular problems, diabetes, obesity, or major cancer diseases, nor was there any dementia in their families. Some of the subjects had skin cancers that were treated; they were considered eligible for the study. Most of the subjects had normal cholesterol levels. While some subjects used walkers to ambulate, they were all very interested in the research, asked intelligent questions, had an active exercise program, and looked quite physically fit. Most had at least college degrees and had higher level positions when they were working.

Normative Aging Study (NAS) Subjects

The VA Normative Aging Study (NAS) is a multidisciplinary longitudinal investigation of the aging process. It was started in the Department of Veteran Affairs in 1963 at the VA outpatient clinic in Boston. The subjects were primarily veterans from World War II and the Korean War. The veterans went through a screening process consisting of three phases, all relating to the health of the participant. From the initial phase of 6,000 men, 2,280 were selected for the study, based on good health and geographic stability. (Women were not available for the study.) The ages of the veterans ranged from 22 to 82 years at the time of entry (average age: 42±9 years). Some 74% were born between 1915 and 1934. Most of the veterans were Caucasian (<2% African American), had a high school diploma (86%), and were from a higher socioeconomic status than the general Boston population. As of 1997, 26% had died, 8% stopped participation, and 6% were lost to follow-up assessment (Brady, C. B., et al., *J Gerontology Series B*, 56:340-346 (2001)).

The veterans in the study had physical exams every 3-5 years which consisted of multiple biomedical parameters, including blood pressure, glucose, and cholesterol levels. In addition to other psychosocial information, many of the veterans had neuropsychological testing, starting in 1993, including the Mini Mental Status exam (MMSE) (Folstein, M. F., et al., *J Psychiatr Res*, 12:189-198 (1975)), and the CERAD battery (word list learning, delayed recall, and figure copying). The stored DNA samples were from approximately 1,200 veterans and included data from their physical exams (blood pressure, glucose, homocysteine, and cholesterol) as well as results from cognitive testing. Of a closely followed subgroup of 1,088 veterans, 94 had an MMSE<23; 294 had MI; 57 had strokes; 437 had cancer; 201 had diabetes; 5 had Parkinson's disease. Of the remainder with MMSE>24, 367 were <65 years of age; 362 were 65-70; 352 were 70-79; 89 were >79 years of age. We have analyzed the group over age 80 with known MMSE's>25 and normal cognitive assessments. Moreover, the medical information on cholesterol, homocysteine, glucose levels, blood pressure readings, were normal and there was no evidence of diabetes, cancer, or cardiovascular problems.

Alzheimer's Patients

The samples consist of 227 Alzheimer's patients. The clinical diagnosis of probable Alzheimer's disease was made according to NINCDS-ADRDA criteria (McKhann, G., et al., Neurology, 34: 939-944 (1984)), after a review of the medical records to verify a documented progressive decline in cognition and appropriate blood work to rule out other medical conditions, including thyroid and vitamin B12 deficiencies. In addition to these criteria, we also included a CT scan and/or MRI of the brain which showed cortical atrophy but no evidence of strokes or tumors. The patients were Caucasian, of European descent.

All participants or the authorized representatives of the patients gave consent for the study, in accordance with the Institutional Review Board guidelines.

The successful aging samples and those from the NAS study were analyzed together for population stratification with Structure 2.1; no significant differences were found for the data (Falush, D., et al., Genetics, 164:1567-1587 (2003)). Thus both groups were classified as the successful aging without cognitive decline (SA). There was no population stratification in the Alzheimer's subjects.

Genotyping

Genomic DNA was extracted using the Qiagen Q1Aamp DNA blood midi kit (Qiagen, Inc., Valencia, Calif.) and suspended in low EDTA TE buffer. Aliquots were quantitated using the NanoDrop spectrophotometer (NanoDrop Technologies, Wilmington, Del.). Samples (14 Alzheimer's patients from three extended families, 29 SA subjects, and 16 spouses and unaffected siblings from the three extended families) were diluted to 50 ng/µl and sent to Precision Biomarker Resources, Inc., (Evanston, Ill.) for genotyping, according to the manufacturers specifications (Affymetrix, Santa Clara, Calif.), using the GeneChip® 500K Mapping Array Set, consisting of two arrays (Nsp I, ~262,000 SNPs and Sty I, ~238,000 SNPs). Genotype calls were obtained from the Bayesian Robust Linear Model with Mahalanobis distance classifier genotype calling algorithm (BRLMM) on the Affymetrix platform. Among the 500,568 SNPs on the microarrays, 469,218 had call rates ≧95% and HWE (Hardy-Weinberg equilibrium) P>0.001, and were further analyzed. Gender calls were in accordance with the X chromosome genotype data and the known gender. Genotypic association was performed using the trial version of HelixTree software (Golden Helix, Bozeman, Mont.). Bonferroni corrections for multiple testing were made using the total number of samples on each array. For stage 2 of the project, additional SNPs in the gene, LRP1B, were selected from the NCBI SNP database. Three of the most significant SNPs from the microarray data and those seven in other LD blocks spanning the gene were selected from the database and were genotyped in the successful aging samples (32 samples) and in the Alzheimer's patients (227 subjects), using fluorescent-detected single base extension with the SNaPshot® Multiplex kit (Applied Biosystems, Foster City, Calif.) as described (Huang, R., and Poduslo, S. E., J Med Genet, 43:e42 (2006)). Power analysis for the 227 Alzheimer's patients and the 32 SA subjects, using G*Power, was 0.84 (Purcell, S, et al., Bioinformatics, 19:149-150 (2003)). For stage 3, 10 additional SNPs in the 4 LD blocks surrounding the most significant SNPs from the database were selected. The trial version of HelixTree® was used to determine the haplotypes and SAS was used for the genotypic, allelic, and haplotype association analysis.

Results

The results from the microarrays indicated that there were three SNPs in a single gene that were significant (P), after Bonferroni correction (bP), when the Successful Aging samples were analyzed versus the Alzheimer's patients (Table I).

TABLE I

| Successful Aging Versus Alzheimer's Disease | | | | | | |
|---|---|---|---|---|---|---|
| Probe set ID | db SNP | Chromosome | Position | P | aP | bP |
| A-1824685 | rs12474609 | 2q22.1 | 141,446,369 | 5.93E−09 | 4.44E−08 | 2.45E−05 |
| A-4234192 | rs10201482 | 2q22.1 | 141,446,369 | 4.95E−06 | 9.09E−04 | 2.73E−03 |
| A-1965117 | rs980286 | 2q22.1 | 141,447,731 | 1.80E−07 | 1.22E−06 | 6.70E−04 |

P, raw P-value; aP, adjusted P-value; bP, Bonferroni-adjusted P-value.

The SNPs are located in the gene, low density lipoprotein-related protein 1B (LRP1B). The gene belongs to the low density lipoprotein receptor gene family. The gene is large, 1,906.41 kb, and has 93 introns.

For stage 2 of the analysis, these three SNPs plus 6 SNPs in other LD blocks spanning the large gene were selected for further analysis, again using the Successful Aging samples (32 samples) versus the Alzheimer's patients (227 samples). The additional SNPs included rs12467730, rs11901880, rs12466938, rs6748626 rs28483746, rs12474609 rs10201482, rs980286, rs13007735. After analysis in stage 2, the SNPs from the microarray were still the most significant, indicating that this area of the gene was of interest. By chi-square analysis, the P values for rs12474609, rs10201482, and rs980286 were P=0.0042, 0.0009, and 0.009, respectively. Haplotype analysis of the three SNPs: T:C:T, gave a P=0.0034.

Encouraged by these results, 10 additional SNPs in four adjacent LD blocks around the SNPs from the microarray were selected for further analysis, to verify this region of interest. The additional SNPs included rs6732847, rs12053560, rs13016717, rs1346641 rs10928081, rs716000, rs716001, rs15845065, rs11888460, rs11904038.

The allelic comparisons and haplotypes are presented in Table II. The SNPs were in four linkage disequilibrium (LD)

blocks, according to HAPMAP. LD was defined as having a pairwise D'=0.92, instead of the usual 0.95. Those SNPs with a minor allele frequency (MAF)<10% were excluded. In addition to the Successful Aging samples, data was also obtained for the CEPH (Foundation Jean Dausset-Centre d'Etude du Polymorphisme Humain; subjects from the NCBI website, and both were analyzed versus the AD samples and versus each other (Table II).

TABLE II

Successful Aging Versus Alzheimer's Disease Versus CEPH Controls

| SNP | AD | SA | CEPH | P SA/AD | Odds ratio | 95% CI |
|---|---|---|---|---|---|---|
| Block 1 |||||||
| rs6732847 |||||||
| C | 253 (62%) | 51 (80%) | 135 (75%) | 0.0069 | 0.42 | 0.22-0.80 |
| T | 153 (38%) | 13 (20%) | 45 (25%) ||||
| rs12053560 |||||||
| C | 46 (11%) | 11 (17%) | 27 (15%) | 0.1822 | 0.62 | 0.30-1.26 |
| T | 360 (89%) | 53 (83%) | 153 (85%) ||||
| rs6748626 |||||||
| G | 336 (83%) | 60 (94%) | n/a | 0.0248 | 0.32 | 0.11-0.91 |
| T | 70 (17%) | 4 (6%) | n/a ||||
| Haplotype |||||||
| CTG ||| | 0.0012 | 0.36 | 0.19-0.68 |
| Block 2 |||||||
| rs13016717 |||||||
| A | 347 (85%) | 55 (86%) | 157 (87%) | 0.9209 | 0.96 | 0.45-2.05 |
| G | 59 (15%) | 9 (14%) | 23 (13%) ||||
| rs1346641 |||||||
| T | 316 (78%) | 52 (81%) | 144 (80%) | 0.5376 | 0.81 | 0.41-1.58 |
| G | 90 (22%) | 12 (19%) | 36 (20%) ||||
| rs10928081 |||||||
| C | 348 (86%) | 62 (97%) | 158 (88%) | 0.0129 | 0.19 | 0.05-0.81 |
| T | 58 (14%) | 2 (3%) | 22 (12%) ||||
| rs12474609 |||||||
| A | 323 (80%) | 68 (94%) | 152 (86%) | 0.0031 | 0.23 | 0.08-0.66 |
| T | 81 (20%) | 4 (6%) | 24 (14%) ||||
| Haplotype |||||||
| ATCA ||| | 0.0052 | 0.43 | 0.23-0.79 |
| Block 3 |||||||
| rs716000 |||||||
| G | 361 (89%) | 62 (97%) | 160 (89%) | 0.0485 | 0.26 | 0.06-1.09 |
| A | 45 (11%) | 2 (3%) | 20 (11%) ||||
| rs716001 |||||||
| C | 307 (76%) | 60 (94%) | 120 (67%) | 0.0016 | 0.22 | 0.08-0.61 |
| A | 95 (24%) | 4 (6%) | 60 (33%) ||||
| rs10201482 |||||||
| G | 298 (73%) | 66 (92%) | 143 (79%) | 0.0008 | 0.25 | 0.11-0.60 |
| C | 108 (27%) | 5 (8%) | 37 (21%) ||||
| rs980286 |||||||
| G | 303 (75%) | 63 (88%) | 141 (79%) | 0.0175 | 0.42 | 0.20-0.88 |
| T | 103 (25%) | 9 (12%) | 37 (21%) ||||
| Haplotype |||||||
| GCGG ||| | 0.0037 | 0.36 | 0.18-0.74 |
| Block 4 |||||||
| rs16845065 |||||||
| G | 342 (84%) | 55 (86%) | 157 (87%) | 0.7269 | 0.87 | 0.41-1.86 |
| C | 64 (16%) | 9 (14%) | 23 (13%) ||||
| rs11888460 |||||||
| T | 362 (89%) | 62 (97%) | 162 (90%) | 0.0536 | 0.27 | 0.06-1.12 |
| G | 44 (11%) | 2 (3%) | 18 (10%) ||||
| rs11904038 |||||||
| C | 300 (74%) | 58 (91%) | 143 (79%) | 0.0035 | 0.29 | 0.12-0.70 |
| T | 106 (26%) | 6 (9%) | 37 (21%) ||||

TABLE II-continued

Successful Aging Versus Alzheimer's Disease Versus CEPH Controls

| | | | | | | |
|---|---|---|---|---|---|---|
| rs13007735 | | | | | | |
| G | 266 (66%) | 53 (74%) | 123 (69%) | 0.1791 | 0.68 | 0.39-1.20 |
| A | 140 (34%) | 19 (26%) | 55 (31%) | | | |
| Haplotype | | | | | | |
| GTCG | | | | 0.0136 | 0.4756 | 0.26-0.87 |

| SNP | P SA/CEPH | OR | 95% CI | P AD/CEPH | OR | 95% CI |
|---|---|---|---|---|---|---|
| Block 1 | | | | | | |
| rs6732847 | | | | | | |
| C | | | | | | |
| T | 0.57 | 1.3 | 0.65-2.22 | 0.0027 | 0.55 | 0.37-0.82 |
| rs12053560 | | | | | | |
| C | | | | | | |
| T | 0.17 | 1.18 | 0.55-2.53 | 0.21 | 0.72 | 0.43-1.21 |
| rs6748626 | | | | | | |
| G | | | | | | |
| T | | | | | | |
| Haplotype | | | | | | |
| CTG | | | | | | |
| Block 2 | | | | | | |
| rs13016717 | | | | | | |
| A | | | | | | |
| G | 0.07 | 0.9 | 0.39-2.05 | 0.32 | 0.86 | 0.51-1.45 |
| rs1346641 | | | | | | |
| T | | | | | | |
| G | 0.05 | 1.08 | 0.52-2.24 | 0.35 | 0.88 | 0.57-1.35 |
| rs10928081 | | | | | | |
| C | | | | | | |
| T | 0.04 | 4.32 | 0.99-18.91 | 0.5 | 0.84 | 0.49-1.41 |
| rs12474609 | | | | | | |
| A | | | | | | |
| T | 0.07 | 2.68 | 0.9-8.04 | 0.065 | 0.63 | 0.38-1.03 |
| Haplotype | | | | | | |
| ATCA | 0.07 | 0.66 | 0.42-1.04 | 0.066 | 0.8 | 0.62-1.02 |
| Block 3 | | | | | | |
| rs716000 | | | | | | |
| G | | | | | | |
| A | 0.06 | 3.88 | 0.88-17.07 | 1 | 1 | 0.57-1.75 |
| rs716001 | | | | | | |
| C | | | | | | |
| A | 0.0001 | 7.5 | 2.6-21.62 | 0.014 | 1.62 | 1.10-2.38 |
| rs10201482 | | | | | | |
| G | | | | | | |
| C | 0.01 | 3.42 | 1.28-9.09 | 0.12 | 0.71 | 0.47-1.09 |
| rs98028 | | | | | | |
| G | | | | | | |
| T | 0.13 | 1.84 | 0.84-4.03 | 0.23 | 0.77 | 0.50-1.18 |
| Haplotype | | | | | | |
| GCGG | <0.001 | 3.43 | 2.10-5.59 | 0.92 | 0.99 | 0.80-1.22 |
| Block 4 | | | | | | |
| rs16845065 | | | | | | |
| G | | | | | | |
| C | 0.07 | 0.9 | 0.39-2.05 | 0.35 | 0.78 | 0.47-1.31 |
| rs11888 | | | | | | |
| T | | | | | | |
| G | 0.08 | 3.44 | 0.78-15.28 | 0.76 | 0.91 | 0.51-1.63 |

TABLE II-continued

Successful Aging Versus Alzheimer's Disease Versus CEPH Controls

| | | | | | | |
|---|---|---|---|---|---|---|
| rs11904038 | | | | | | |
| C | | | | | | |
| T | 0.04 | 2.5 | 1.00-6.24 | 0.15 | 0.73 | 0.48-1.12 |
| rs13007 | | | | | | |
| G | | | | | | |
| A | 0.48 | 1.25 | 0.68-2.3 | 0.4 | 0.85 | 0.58-1.24 |
| Haplotype | | | | | | |
| GTCG | 0.07 | 1.44 | 0.97-2.15 | 0.07 | 0.82 | 0.65-1.02 |

AD, Alzheimer's samples; SA, successful aging without cognitive decline; CEPH, European samples, data obtained from the NCBI website; OR, odds ratio; n/a, not available.

The haplotypes for the Alzheimer's samples versus the Successful Aging without cognitive decline samples from the four LD blocks all have significant P values, ranging from 0.0012 to 0.0136, with low odds ratios ranging from 0.36 to 0.48. Thus the haplotype from Block 1 has P=0.0012; from Block 2, P=0.0052; from Block 3, P=0.0037; and Block 4, P=0.0136. The frequencies for the AD, CEPH, and SA for the haplotype in Block 1 were 78%, 80%, and 85%; for Block 2, they were 82%, 85%, and 89%; for Block 3, 78%, 79%, and 93%; for Block 4, 78%, 81%, and 86%, respectively. When the Alzheimer's samples versus the CEPH samples were analyzed, none of the haplotype blocks were significant. This area of the gene, LRP1B, has genetic variants significant/protective for successful aging without cognitive decline. Interestingly, 80% of the successful aging subjects were APOE3 and only 10% were APOE 2, suggesting that in this group of subjects, APOE 2 may be less important for protection against AD. Of the 10% who were APOE 4, only one was APOE 4/4. The Alzheimer's patients were 43% APOE 4, 54% APOE 3, and 3% APOE 2.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for identifying a human subject with an increased chance of reaching 85 without developing cognitive decline comprising: assaying a biological sample obtained from the human subject to determine the nucleotide present at the polymorphic position of rs12474609 of the low density lipoprotein related protein 1B (LRP1B) gene; and identifying that the human subject with one or more A alleles at the polymorphic position of rs12474609 has an increased chance of reaching age 85 without developing cognitive decline in comparison to a human subject with two T alleles at the polymorphic position of rs12474609.

2. The method of claim 1, wherein the assaying is carried out by a process selected from the group consisting of direct sequencing, allele-specific probe hybridization, allele-specific primer extension, allele-specific amplification, sequencing, 5' nuclease digestion, molecular beacon assay, oligonucleotide ligation assay, size analysis, and single-stranded conformation polymorphism.

* * * * *